(12) United States Patent
Yamamoto (10) Patent No.: US 8,044,364 B2
(45) Date of Patent: Oct. 25, 2011

(54) DOSIMETRY DEVICE FOR CHARGED PARTICLE RADIATION (75) Inventor: Yuichi Yamamoto, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 378 days.

(21) Appl. No.: 11/713,698

(22) Filed: Mar. 5, 2007

(65) Prior Publication Data

US 2008/0061245 A1 Mar. 13, 2008

(30) Foreign Application Priority Data

Sep. 8, 2006 (JP) ................. 2006-244119

(51) Int. Cl.
H01J 47/02 (2006.01)
(52) U.S. Cl. ......... 250/378; 250/374; 250/375; 250/389
(58) Field of Classification Search ............ 250/374, 250/375, 378, 389
See application file for complete search history.

(56) References Cited

U.S. PATENT DOCUMENTS

| 4,500,785 | A | * | 2/1985 | Whetten et al. | 250/385.1 |
|---|---|---|---|---|---|
| 5,308,988 | A | | 5/1994 | Siedband | |
| 7,003,076 | B2 | * | 2/2006 | Okumura et al. | 378/98.8 |
| 2002/0054659 | A1 | | 5/2002 | Okumura et al. | |
| 2002/0134945 | A1 | | 9/2002 | Tanimori et al. | |
| 2003/0029989 | A1 | * | 2/2003 | Stettner et al. | 250/208.1 |

FOREIGN PATENT DOCUMENTS

| CN | 1308487 | 8/2001 |
|---|---|---|
| JP | 03-209795 | 9/1991 |
| JP | 2002-006047 | 1/2002 |
| JP | 2003-066149 | 3/2003 |
| JP | 2004-065285 A | 3/2004 |

OTHER PUBLICATIONS

R. Bonin et al., "A pixel chamber to monitor the beam performances in hadrontherapy", Nuclear Instruments and Methods in Physics Research, A519 (2004), pp. 674-686. (Listed on p. 1 of the specification).
Office Action dated Jul. 9, 2010 in a corresponding German patent application, 3 pages.

* cited by examiner

Primary Examiner — David Porta
Assistant Examiner — Hugh H Maupin
(74) Attorney, Agent, or Firm — Buchanan Ingersoll & Rooney PC (57) ABSTRACT A dosimetry device for charged particle radiation that can be exclusive of cables and connectors between substrates is provided. A plurality of first electrodes are formed on one surface of a printed circuit board, a second electrode substrate having a second electrode opposing each of the plurality of first electrodes through an ionized space is provided, and a signal processing circuit is provided on the other surface opposing the surface of the printed circuit board. The signal processing circuit includes at least one amplifying circuit, a plurality of integrating capacitors corresponding to the amplifying circuit for integrating charge at each corresponding one of the first electrodes, and at least one selector switch that switchably connects each of the integrating capacitors to the amplifying circuit. The printed circuit board may be a multi-layer printed circuit board.

20 Claims, 8 Drawing Sheets

DOSIMETRY DEVICE FOR CHARGED PARTICLE RADIATION

BACKGROUND OF THE INVENTION

1. Field of the Invention

The present invention relates to a dosimetry device used to measure the dose distribution of charged particle radiation.

2. Description of the Related Art

A conventional dosimetry device for charged particle radiation is disclosed for example in "A pixel chamber to monitor the beam performances in hadrontherapy," *Nuclear Instruments and Methods in Physics Research*, A519, pp. 674 to 686, 2004.

The dosimetry device for charged particle radiation disclosed by the publication includes a high voltage electrode (cathode electrode), an ionization chamber including a spacing frame and a frame having a plurality of anode electrodes arranged in a matrix, and a signal processing circuit that processes a signal from each of the anode electrodes. An ionized space forms between the high voltage electrode (cathode electrode) and each of the anode electrodes, and high voltage is applied between the high voltage electrode (cathode electrode) and each of the anode electrodes through the ionized space. When charged particles enter the ionized space, the air inside the ionized space is excited and ions are generated, the ions are attracted by corresponding anode electrodes, and charge is generated at the anode electrode. The charge at each of the anode electrodes can be read by the signal processing circuit to measure the dose distribution of the charged particles in the ionized space.

SUMMARY OF THE INVENTION

In the dosimetry device for charged particle radiation disclosed by the publication, the signal processing circuit is provided on a substrate different from the frame in which the anode electrodes are provided. Therefore, the frame having the anode electrodes and the substrate having the signal processing circuit thereon must be connected by cables and connectors, and in consideration of the connector size and a practical number of cables required, the number of anode electrodes cannot be increased, in other words, the resolution of the dose distribution cannot be increased. The substrate on which the frame having the anode electrodes is provided and the substrate having the signal processing circuit thereon are necessary in total, which increases the number of substrates and the cost.

According to the invention, a low cost dosimetry device for charged particle radiation exclusive of such cables and connectors is provided.

A dosimetry device for charged particle radiation according to a first aspect of the invention has a printed circuit board and includes a plurality of first electrodes formed on one surface of the printed circuit board, a second electrode substrate having a second electrode opposing to each of the first electrodes through an ionized space, and a signal processing circuit on the other surface opposing to the surface of the printed circuit board. The signal processing circuit includes a plurality of integrating capacitors for integrating charge at each of the first electrodes, at least one amplifying circuit, and at least one selector switch that switchably connects each corresponding one of the integrating capacitors to the amplifying circuit.

A dosimetry device for charged particle radiation according to a second aspect of the invention has a multi-layer printed circuit board, the multi-layer printed circuit board has a plurality of wiring layers opposing to one another, the device includes a plurality of first electrodes formed on one surface of one of the wiring layers positioned on one surface of the multi-layer printed circuit board among the plurality of wiring layers, a second electrode substrate having a second electrode opposing to each of the first electrodes through an ionized space, and a signal processing circuit provided in at least another one of the wiring layers of the multi-layer printed circuit board. The signal processing circuit includes a plurality of integrating capacitors for integrating charge at each of the first electrodes, at least one amplifying circuit, and at least one selector switch that switchably connects each corresponding one of the integrating capacitors to the amplifying circuit.

In the dosimetry device for charged particle radiation according to the first aspect of the invention, a plurality of first electrodes are formed on one surface of the printed circuit board, a second electrode substrate having a second electrode is provided opposing to each of the first electrodes through an ionized space, and a signal processing circuit is provided on the other surface opposing to one surface of the printed circuit board. The signal processing circuit includes a plurality of integrating capacitors for integrating charge at each of the first electrodes, at least one amplifying circuit, and at least one selector switch that switchably connects each corresponding one of the integrating capacitors to the amplifying circuit. Therefore, it is not necessary to use special cables and connectors between the plurality of first electrodes and the signal processing circuit, and a low cost dosimetry device for charged particle radiation can be provided.

In the dosimetry device for charged particle radiation according to the second aspect of the invention, a multi-layer printed circuit board has a plurality of wiring layers opposing to one another, a plurality of first electrodes are formed on one surface of one of the wiring layers positioned on one surface of the multi-layer printed circuit board among the plurality of wiring layers, a second electrode substrate having a second electrode is provided opposing to each of the first electrodes through an ionized space, and a signal processing circuit is provided on at least another one of the wiring layers of the multi-layer printed circuit board. The signal processing circuit includes a plurality of integrating capacitors for integrating charge at each of the first electrodes, at least one amplifying circuit, and at least one selector switch that switchably connects each corresponding one of the integrating capacitors to the amplifying circuit. Therefore, it is not necessary to use special cables and connectors between the plurality of first electrodes and the signal processing circuit, and a low cost dosimetry device for charged particle radiation can be provided.

The foregoing and other objects, features, aspects, and advantages of the present invention will be become more apparent from the following detailed description of the present invention when taken in conjunction with the accompanying drawings.

DETAILED DESCRIPTION OF THE PREFERRED EMBODIMENTS

Now, several embodiments of the invention will be described in conjunction with the accompanying drawings.

First Embodiment

Figure 1:
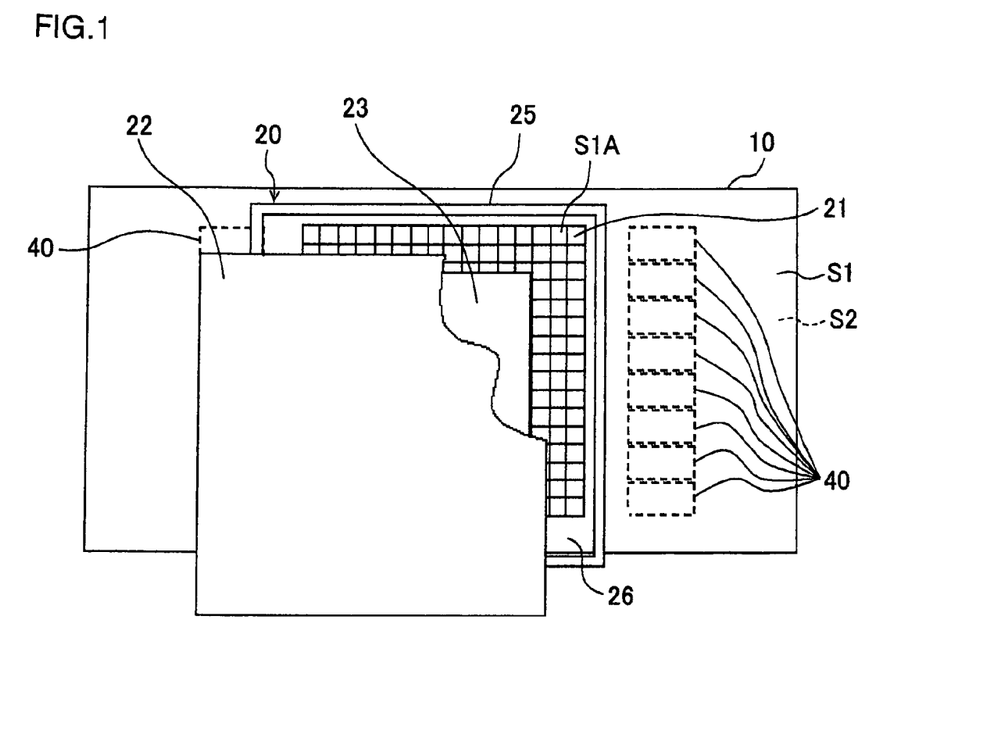
FIG. 1 is a view of a dosimetry device for charged particle radiation according to a first embodiment of the invention.
Figure 2:
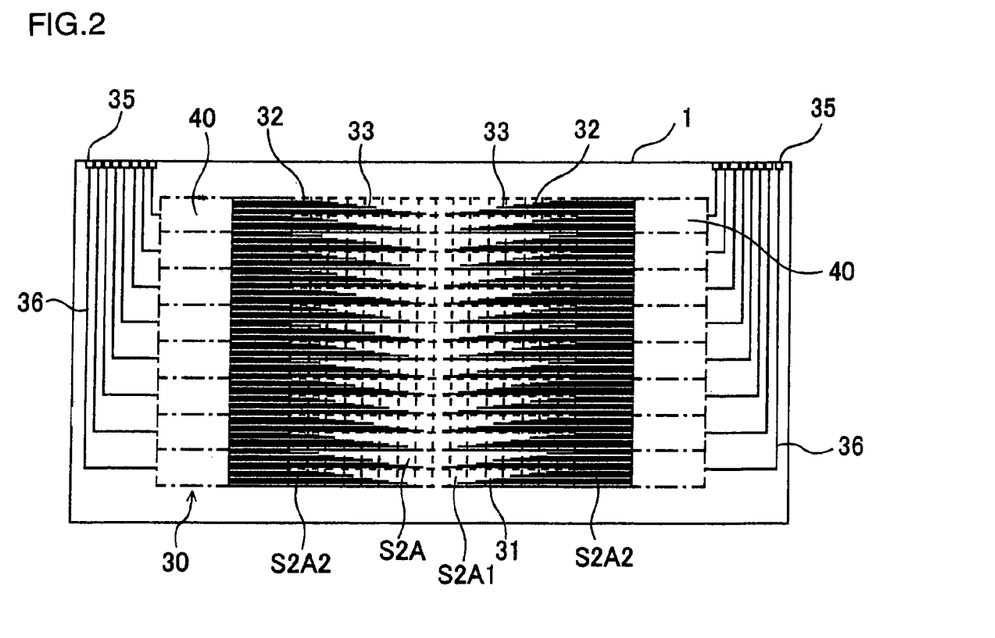
FIG. 2 is a backside view of FIG. 1.
Figure 3:
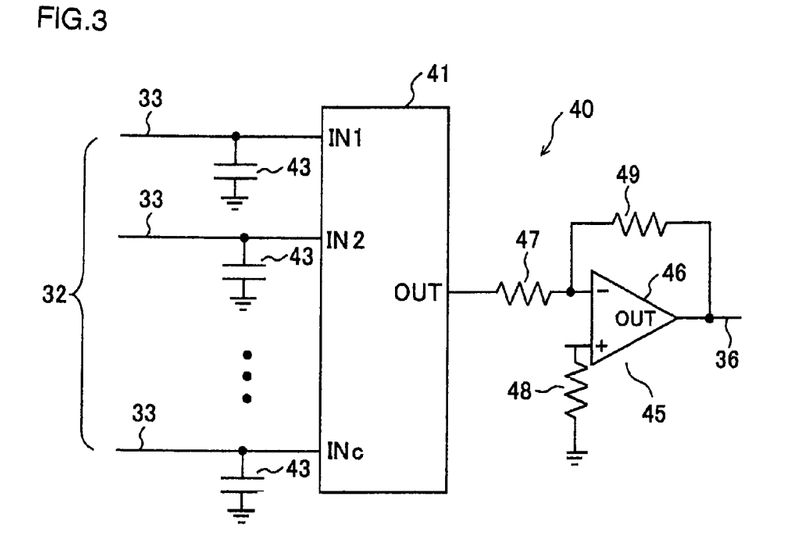
FIG. 3 is an electrical circuit diagram of one signal processing block in a signal processing circuit according to the first embodiment.

FIG. 1 is a view of a dosimetry device for charged particle radiation according to a first embodiment of the invention, FIG. 2 is a backside view of a printed circuit board according to the first embodiment, and FIG. 3 is an electrical circuit diagram of one signal processing block in a signal processing circuit according to the first embodiment.

With reference to FIG. 1, a single printed circuit board (PCB) 10 is used for the dosimetry device for charged particle radiation according to the first embodiment. The printed circuit board 10 has a pair of main surfaces S1 and S2 opposing to each other. The main surface S1 is for example a front surface of the printed circuit board 10, and the main surface S2 is the backside surface thereof. The printed circuit board 10 is a double-sided printed circuit board, and circuit elements are formed both on the main surfaces S1 and S2.

An ionization unit 20 is provided on the main surface S1 of the printed circuit board 10, and a signal processing circuit 30 is provided on the main surface S2. The ionization unit 20 includes a plurality of first electrodes 21, a second electrode substrate 22, and a spacing frame 25. The plurality of first electrodes 21 are for example anode electrodes provided in a matrix on the central region S1A of the main surface S1. The spacing frame 25 is fixed to the main surface S1 to surround the central region S1A. The spacing frame 25 is a frame member in a square shape made of an insulating material and surrounds the central region S1A of the main surface S1 and the plurality of first electrodes 21. The spacing frame 25 has a prescribed thickness in the direction vertical to the main surface S1.

The second electrode substrate 22 is fixed on the spacing frame 25. The second electrode substrate 22 has an outside size substantially equal to the outside size of the spacing frame 25, has its peripheral part fixed on the spacing frame 25, and forms the sealed ionized space 26 inside. The ionized space 26 is formed between the central region S1A of the main surface S1 and the second electrode substrate 22, and its outer circumference is sealed by the spacing frame 25. The second electrode substrate 22 has a second electrode 23 attached thereto. The second electrode 23 is for example a cathode and opposes to the plurality of first electrodes 21 through the ionized space 26.

In the ionization unit 20, the ionized space 26 is formed between the second electrode 23 and each of the first electrodes 21, and high voltage is applied between the second electrode 23 and each of the first electrodes 21 across the ionized space 26. Charged particle radiation to be measured is directed at the ionized space 26 through the second electrode substrate 22. When charged particles enter the ionized space 26, the air inside the ionized space 26 is excited and ions are generated. The ions are each attracted to a corresponding one of the first electrodes 21, and charge is generated at the first electrode 21. The charge at each of the first electrodes 21 is read by the signal processing circuit 30, so that the dose distribution of the charged particles in the ionized space 26 can be measured.

As shown in FIG. 2, the signal processing circuit 30 includes a wiring block 31, a plurality of external terminals 35, and a plurality of signal processing blocks 40. The wiring block 31 is provided in the central region S2A of the main surface S2 of the printed circuit board 10. The central region S2A of the main surface S2 has a first part S2A1 that overlaps the central region S1A of the main surface S1 and a pair of second parts S2A2 on both sides of the first part S2A1 that do not overlap the central region S1A but are positioned outside the region. The wiring block 31 is formed across the first part S2A1 and the second parts S2A2. The plurality of signal processing blocks 40 are provided on both sides of the wiring blocks 31. The plurality of external terminals 35 are for example provided on both sides of the upper end of the printed circuit board 10 and connected to the signal processing blocks 40 by wirings 36.

The wiring block 31 connects the plurality of first electrodes 21 and the plurality of signal processing blocks 40. The signal processing blocks 40 are connected to different first electrodes 21 and the first electrodes 21 are each connected to any one of the plurality of signal processing circuits 40. More specifically, if the number of the plurality of first electrodes 21 is A and the number of the plurality of signal processing blocks 40 is B, the signal processing blocks 40 are each connected to C different first electrodes 21 (C=A/B). Stated differently, the A first electrodes are divided into B combinations, and the combinations each include C first electrodes 21, and the C first electrodes 21 included in each of the B combinations are connected to one of the different signal processing blocks 40.

The wiring block 31 includes a plurality of wiring combinations 32. The number of the wiring combinations 32 is equal to the number B of the signal processing blocks 40. The plurality of the wiring combinations 32 are connected to the plurality of signal processing blocks 40 and connect the plurality of signal processing blocks 40 to C first electrodes 21 corresponding to them. The wiring combinations 32 each include C wirings 33 and the C wirings 33 are connected to corresponding C first electrodes 21. The C wirings 33 extend at the backside surfaces of the corresponding C first electrodes 21 and are connected to the corresponding C first electrodes 21 at the backside surfaces through the printed circuit board 10. The plurality of signal processing blocks 40 are each connected to a corresponding one of external terminals 35 through one wiring 36.

FIG. 3 is a diagram of a part of the signal processing circuit 30 showing one signal processing block 40 and one wiring combination 32 connected to the block. Each of the plurality of signal processing blocks 40 has the configuration shown in FIG. 3. As shown in FIG. 3, each of the signal processing blocks 40 include a selector switch 41, a plurality of integrating capacitors 43, and an amplifying circuit 45.

The selector switch 41 has C input terminals IN1, IN2, and INc, and one output terminal OUT. The C wirings 33 included in each combination 32 are connected to the input terminals IN1, IN2, . . . , and INc of the selector switch 41, respectively. The number of the integrating capacitors 43 is equal to the number C of the wirings 33. The C integrating capacitors 43 are connected to a circuit that grounds the input terminals IN1, IN2, . . . , and INc of the selector switch 41. The integrating capacitors 43 each integrate and hold charge at a corresponding one of the C first electrodes 21. The number of the integrating capacitors 43 corresponding to one signal processing block 40 is equal to the number C of the wirings 33, while the C integrating capacitors 43 are connected corresponding to each of the B signal processing blocks 40, and therefore the signal processing circuit 30 includes A=B×C integrating capacitors 43, each of which is connected to a corresponding one of the A first electrodes 21.

The integrating capacitors 43 are each provided in the second part S2A2 in the central region S2A in which the wiring block 31 is provided. The second parts S2A2 do not overlap the central region S1A of the main surface S1 having the plurality of first electrodes 21 thereon, and therefore charged particle radiation is not directed thereon. Therefore, the integrating capacitors 43 are not affected by charged particle radiation and integrate and hold the charge at the corresponding first electrodes 21.

The amplifying circuit 45 has an operational amplifier 46 and three resistors 47, 48, and 49. The operational amplifier 46 has a negative input, a positive input, and an output OUT. The negative input of the operational amplifier 46 is connected to the output terminal OUT of the selector switch 41 through the resistor 47. The resistor 48 is connected to the circuit that grounds the positive input of the operational amplifier 46. The resistor 49 is connected between the output OUT and the negative input of the operational amplifier 46 and feeds back the output OUT to the negative input. The output OUT of the operational amplifier 46 is connected to the external terminal 35 by the wiring 36.

The selector switch 41 sequentially switchably connects the input terminals IN1, IN2, . . . , and INc to the output terminal OUT and sequentially supplies charge at the integrating capacitors 43 to the negative input of the operational amplifier 46. The operational amplifier 46 sequentially amplifies the charge of each of the integrating capacitors 43 and sequentially supplies an amplified signal thereof to the external terminal 35. Charge at the first electrodes 21 corresponding to one signal processing block 40 can be read by reading the signals at the external terminal 35.

The plurality of signal processing blocks 40 each have a configuration as shown in FIG. 3 and signals having amplified charge at each corresponding C first electrodes 21 are sequentially output to the corresponding external terminals 35. In this way, the signals having charge at all the first electrodes 21 amplified can be read by reading the signals at all the plurality of external terminals 35 and the dose distribution of the charged particle radiation for the entire ionized space 26 can be measured.

According to the first embodiment, the plurality of first electrodes 21 are formed on the main surface S1 of the printed circuit board 10 and the second electrode substrate 22 having the second electrode 23 opposing the first electrodes 21 through the ionized space 26 is provided. The signal processing circuit 30 is provided on the other main surface S2 opposing the main surface S1 of the printed circuit board 10. The signal processing circuit 30 has at least one signal processing block 40, and the signal processing block 40 includes the plurality of integrating capacitors 43 that integrate charge at the corresponding first electrodes 21, the common amplifying circuit 45 that amplifies the charge at the integrating capacitors 43, and the selector switch 41 that switchably connects the integrating capacitors to the amplifying circuit 45, so that special cables and connectors are not necessary between the plurality of first electrodes 21 and the signal processing circuit 30, and a low cost dosimetry device for charged particle radiation can be provided.

Second Embodiment

Figure 4:
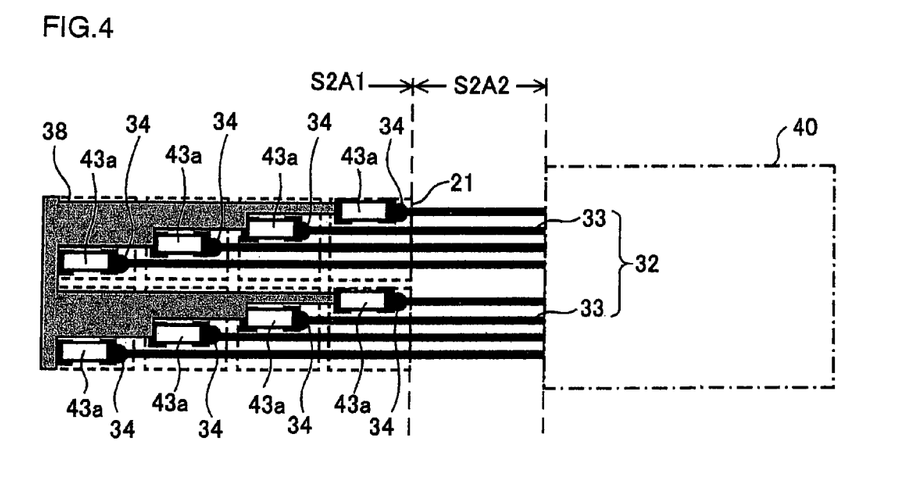
FIG. 4 is a view showing an arrangement of ceramic capacitors in the dosimetry device for charged particle radiation according to a second embodiment of the invention.

According to the first embodiment, the plurality of integrating capacitors 43 connected to the plurality of first electrodes 21 are provided in the second parts S2A2 unaffected by charged particle radiation in the central region S2A of the main surface S2. According to the second embodiment, the plurality of integrating capacitors 43 are ceramic capacitors 43a which are provided in the first part S2A1 of the central region S2A, in other words, at the backside surfaces of the first electrodes 21. The first part S2A1 has the plurality of first electrodes 21 therein, and the ceramic capacitors 43a are subjected to charged particle radiation. However, the ceramic capacitors 43a having high resistance against charged particle radiation can integrate and hold charge at the first electrodes 21 without the effect of the charged particle radiation though they are provided at the backside surfaces of the first electrodes 21.

FIG. 4 is a view showing the arrangement of one signal processing block 40 and a plurality of ceramic capacitors 43a corresponding to the block according to the second embodiment. The ceramic capacitors 43a are each provided at the backside surface of a corresponding one of the first electrodes 21. One wiring combination 32 is provided on the right side of each of the ceramic capacitors 43a, and the wiring combination 32 includes C wirings 33, each of which is connected to a corresponding one of the first electrodes 21. The wirings 33 each connect one electrode of each of the ceramic capacitors 43a to a corresponding one of the first electrodes 21 through a through hole 34 of the printed circuit board 10 formed on the right end of the ceramic capacitor 43a. A ground electrode pattern 38 is formed on the left side of each of the ceramic capacitor 43a. The ground electrode patterns 38 are connected together to the other electrodes of the ceramic capacitors 43a and ground the capacitors 43a.

According to the second embodiment, the backside surfaces of the second electrodes 21 can be used as a space for providing the ceramic capacitors 43a, so that the area occupied by the signal processing blocks 40 can be reduced, the area of the printed circuit board 10 can also be reduced, and the cost can be reduced. Note that the second embodiment has the same configuration as that of the first embodiment other than the arrangement pattern shown in FIG. 4.

Third Embodiment

According to a third embodiment, the printed circuit board 10 according to the first embodiment is replaced by a multi-layer printed circuit board MPCB. The multi-layer printed circuit board MPCB includes number n of wiring layers 51, 52, 53, 54, . . . , 5(n −1), and 5n opposing and parallel to one another. A wiring layer positioned on the main surface S1 of the multi-layer printed circuit board MPCB is referred to as "first wiring layer 51" and a wiring layer positioned on the main surface S2 is referred to as "n-th wiring layer 5n." A plurality of intermediate wiring layers other than the first and n-th wiring layers 51 and 5n are referred to as second wiring layer 52, third wiring layer 53, fourth wiring layer 54, . . . , and (n−1)-th wiring layer 5(n−1) sequentially from the first wiring layer 51 to the n-th wiring layer 5n.

An ionization unit 20 is provided on the main surface S1 of the multi-layer printed circuit board MPCB similarly to the first embodiment. More specifically, a second electrode 23 is provided in the central region S1A of the main surface S1 to oppose to first electrodes 21 through an ionized space 26. The second electrode 23 is attached to one surface of the second electrode substrate 22, which is provided on the main surface S1 through a spacing frame 25.

Figure 5:
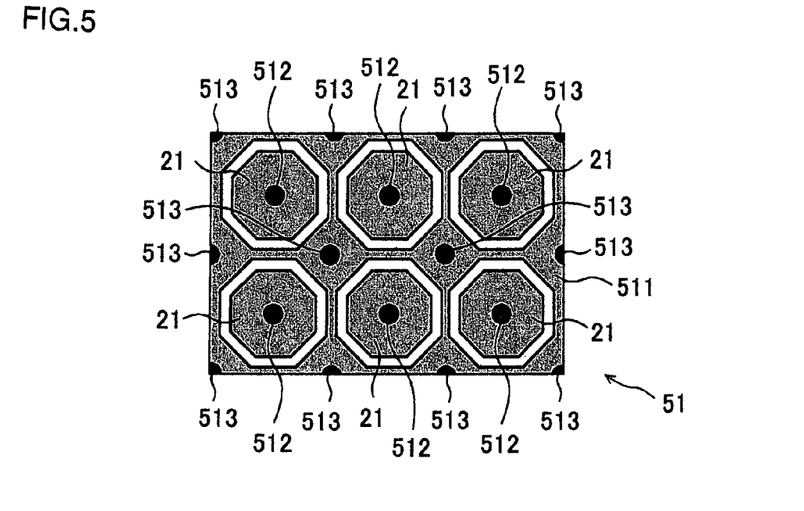
FIG. 5 shows a pattern of a part of a first wiring layer in a dosimetry device for charged particle radiation according to a third embodiment of the invention.
Figure 6:
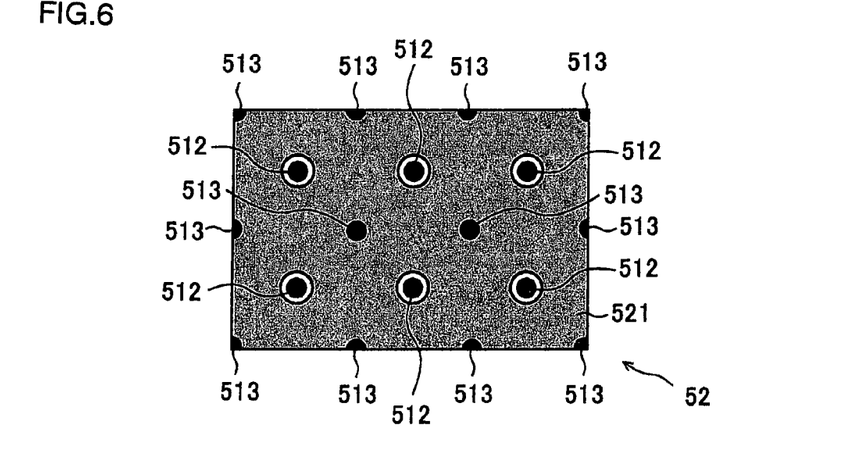
FIG. 6 shows a pattern of a part of a second wiring layer according to the third embodiment.
Figure 7:
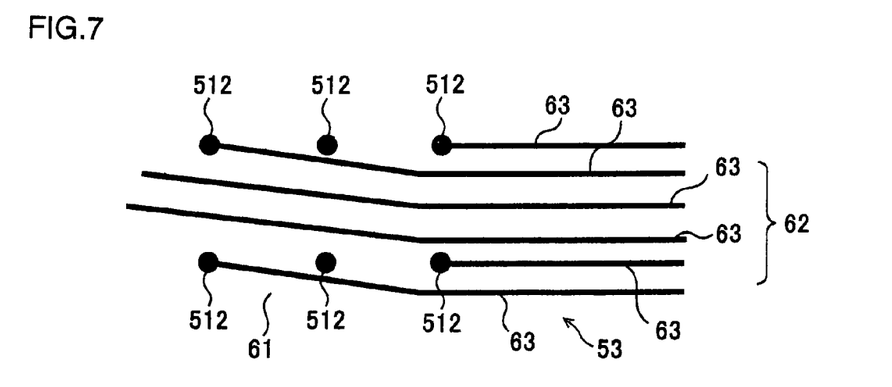
FIG. 7 shows a pattern of a part of a third wiring layer according to the third embodiment.

FIG. 5 shows a part of the first wiring layer 51, FIG. 6 shows a part of the second wiring layer 52, and FIG. 7 shows a part of the third wiring layer 53. On the n-th wiring layer 5n, a plurality of signal processing blocks 40, a plurality of integrating capacitors 43 connected to a plurality of first electrodes 21, and wiring combinations 32 corresponding to the signal processing blocks 40 are provided. As shown in FIG. 3, the signal processing blocks 40 each include a selector switch 41 and an amplifying circuit 45.

As shown in FIG. 5, on the first wiring layer 51, a plurality of first electrodes 21 arranged in a matrix and a ground electrode pattern 511 are formed. The first electrodes 21 oppose to the second electrode 23 through the ionized space 26. The plurality of first electrodes 21 have for example a hexagonal shape, and a first through hole 512 is connected to the center of each of the first electrodes 21. The first through holes 512 penetrate the second wiring layer 52 and extends to the third wiring layer 53, . . . , and the (n−1)-th layer 5(n−1). The ground electrode pattern 511 is formed on the first wiring layer 51 to surround the first electrodes 21. The ground electrode pattern 511 is formed around and with a distance apart from the first electrodes 21 and electrically insulated from the first electrodes 21.

As shown in FIG. 6, a ground electrode pattern 521 is formed in the second wiring layer 52 to surround the first through holes 512. The ground electrode pattern 521 is formed around and with a distance apart from the first through holes 512 and electrically insulated from the through holes 512. The ground electrode pattern 521 formed on the second wiring layer 52 opposes to the ground electrode pattern 511 formed on the first wiring layer 51. The ground electrode patterns 511 and 512 are connected with each other by a plurality of second through holes 513. The second through holes 513 are ground electrode connecting through holes that penetrate through the multi-layer printed circuit board MPCB between the first and second wiring layers 51 and 52 and connect the ground electrode patterns 511 and 521 with each other.

The third wiring layer 53, the fourth wiring layer 54, . . . , the (n−1)-th wiring layer 5(n−1) between the second wiring layer 52 and the n-th wiring layer 5n are each provided with a wiring pattern 61. The wiring patterns 61 connect the signal processing blocks 40 on the n-th wiring layer 5n and the corresponding plurality of first electrodes 21 with one another. These wiring patterns 61 connect different signal processing blocks 40 provided at the n-th wiring layer 5n and C different first electrodes 21 corresponding to the signal processing blocks 40 with one another.

FIG. 7 shows the wiring pattern 61 formed on the third wiring layer 53. The wiring pattern 61 includes a wiring combination 62 and the wiring combination 62 includes C wirings 63. The wirings 63 connect one signal processing block 40 and C first electrodes 21 corresponding to the blocks with one another in the n-th wiring layer 5n. The wirings 63 are connected with the first through holes 512 connected to the C first electrodes 21. A wiring pattern 61 the same as the wiring pattern 61 shown in FIG. 7 is formed in each of the fourth wiring layer 54, . . . , and the (n−1)-th wiring layer 5(n−1).

At the double-sided printed circuit board 10 according to the first embodiment, the wiring combinations 32 in the wiring block 31 are arranged two-dimensionally in the central region S2A of the main surface S2. The wirings 33 in each combination 32 cannot be thinned infinitely, therefore the number B of combinations 32 to be arranged two-dimensionally is limited, and the number A of the first electrodes 21 is limited. The limit for the number A of the first electrodes 21 limits the resolution of the dose distribution of charged particle radiation. In comparison with the first embodiment, a multi-layer printed board MPCB is used according the third embodiment, and the wiring patterns 61 that connect the A first electrodes 21 and the signal processing circuit 30 are scattered among the third wiring layer 53 to the (n−1)-th wiring layer 5(n−1), and therefore the number C of the wirings 63 in each wiring pattern 61 can be increased. Therefore, the area of each of the first electrodes 21 can be reduced, so that the number A of the first electrodes 21 can be increased and the resolution of the dose distribution of charged particle radiation can be increased.

According to the third embodiment, the wiring patterns 61 are scattered among the third wiring layer 53 to the (n−1)-th wiring layer 5(n−1), the wiring patterns 61 can be provided three-dimensionally in regions overlapping each other and yet without contacting each other. Therefore, the relation between the wirings 63 in each wiring pattern 61 and the first electrodes 21 connected thereto can be more flexible in designing, so that the relation between the first electrodes 21 and the signal processing blocks 40 can be set with more flexibility. Therefore, more flexibility can be secured in the circuit design.

According to the third embodiment, the ground patterns 511 and 521 are formed in the first and second wiring layers 51 and 52, so that the effect of external noise can be alleviated by the ground patterns 511 and 521 and the dose distribution of charged particle radiation can be measured with high precision.

Fourth Embodiment

According to a fourth embodiment, the multi-layer printed circuit board MPCB according to the third embodiment is further provided with m additional wiring layers 71, 72, . . . , and 7m. Consequently, according to the fourth embodiment, the multi-layer printed circuit board MPCB has (n+m) wiring layers.

The additional m wiring layers 71, 72, . . . , and 7m are added between the third wiring layer 53 and the n-th wiring layer 5n according to the third embodiment. Stated differently, in the direction from the third wiring layer 53 to the n-th wiring layer 5n, the third wiring layer 53, the additional wiring layer 71, the fourth wiring layer 54, the additional wiring layer 72, . . . , the (n−1)-th wiring layer 5(n−1), the additional wiring layer 7m, and the n-th wiring layer 5n are sequentially provided, in other words, the wiring layers 53, 54, . . . , and 5n and the additional wiring layers 71, 72, . . . , and 7m are alternately provided. According to the fourth embodiment, the second through holes 513 according to the third embodiment penetrate through the third wiring layer 53, the additional wiring layer 71, . . . , and the (n−1)-th wiring layer 5(n−1) and extend to the additional wiring layer 7m. The additional wiring layers 71, 72, . . . , and 7m are each provided with a ground electrode pattern 711 the same as the ground electrode pattern 521 shown in FIG. 6, and the ground electrode patterns 711 are connected with one another through second through holes 513.

Figure 8:
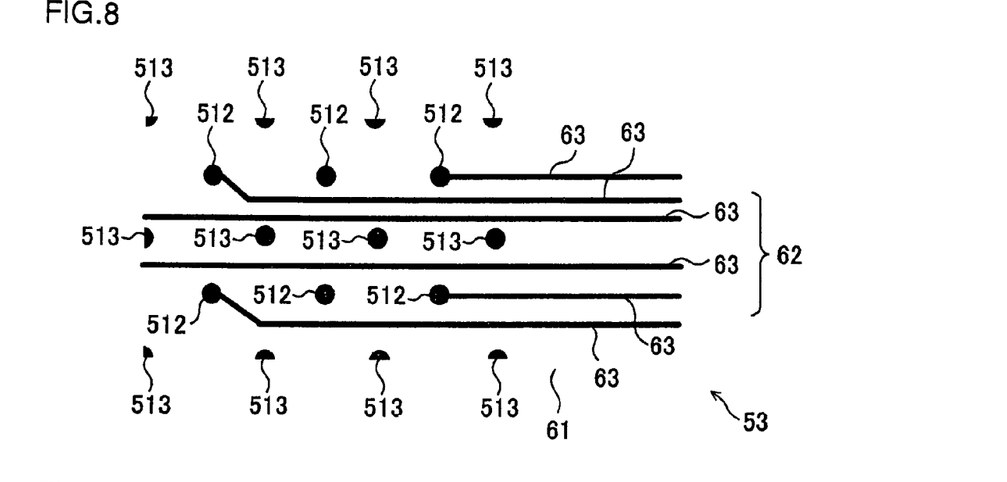
FIG. 8 shows a pattern of a part of a third wiring layer in a dosimetry device for charged particle radiation according to a fourth embodiment of the invention.
Figure 9:
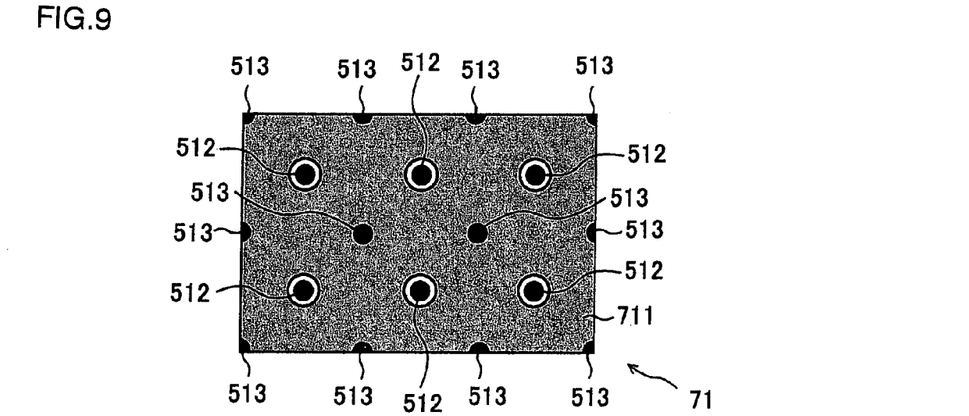
FIG. 9 shows a pattern of a part of an additional wiring layer according to the fourth embodiment.
Figure 10:
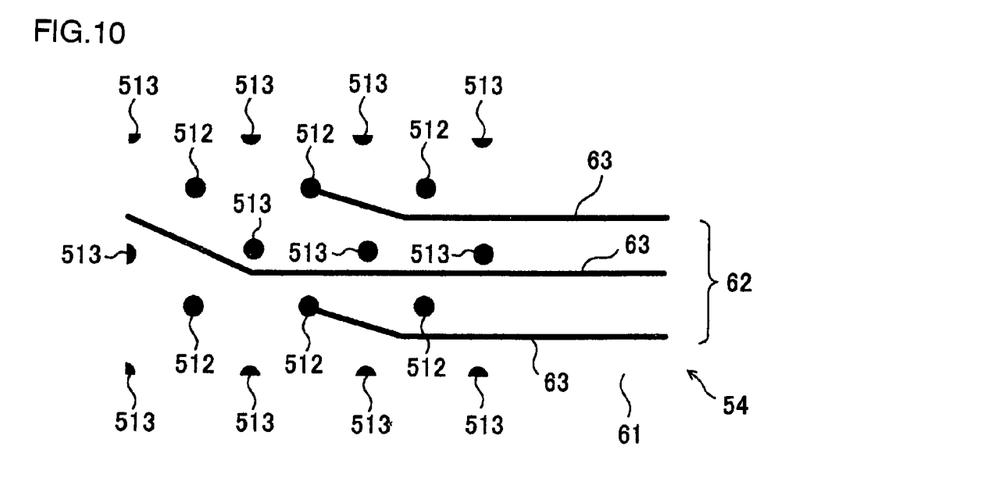
FIG. 10 shows a pattern of a part of a fourth wiring layer according to the fourth embodiment.

FIG. 8 shows a part of the third wiring layer 53 according to the fourth embodiment, FIG. 9 shows a part of the additional wiring layer 71 according to the embodiment, and FIG. 10 shows a part of the fourth wiring layer 54 according to the embodiment. As shown in FIG. 8, the first and second through holes 512 and 513 penetrate the third wiring layer 53. As shown in FIG. 9, the ground electrode pattern 711 is formed in the additional wiring layer 71. The ground electrode pattern 711 is formed to surround the first through holes 512 similarly to the ground electrode pattern 521 in the second wiring layer 52 in FIG. 6.

The ground electrode pattern 711 is formed around and with a distance apart from the first through holes 512 and electrically insulated from the through holes 512. The ground electrode pattern 711 formed in the additional wiring layer 71 is connected to the ground electrode pattern 521 (FIG. 6) formed in the second wiring layer 52 by the second through holes 513. The fourth wiring layer 54 has a wiring pattern 61 as shown in FIG. 10, and the first and second through holes 512 and 513 penetrate therethrough. The wiring pattern 61 is connected with the first through holes 512. The wiring pattern 61 connects the corresponding plurality of first electrodes 21 to the corresponding signal blocks 40 through the first through holes 512.

According to the fourth embodiment, the ground electrode patterns 711 formed in the additional wiring layers 71, 72, . . . , and 7m shield the wiring patterns 61 formed in the third wiring layer 53, the fourth wiring layer 54, . . . , and the (n−1)-th wiring layer 5(n−1) against external noise and the wirings 33 formed in the n-th wiring layer 5n against external noise. Consequently, external noise coming into the wiring patterns 61 and the wirings 33 is reduced, so that the dose distribution of charged particle radiation can be measured more precisely.

Fifth Embodiment

Figure 11:
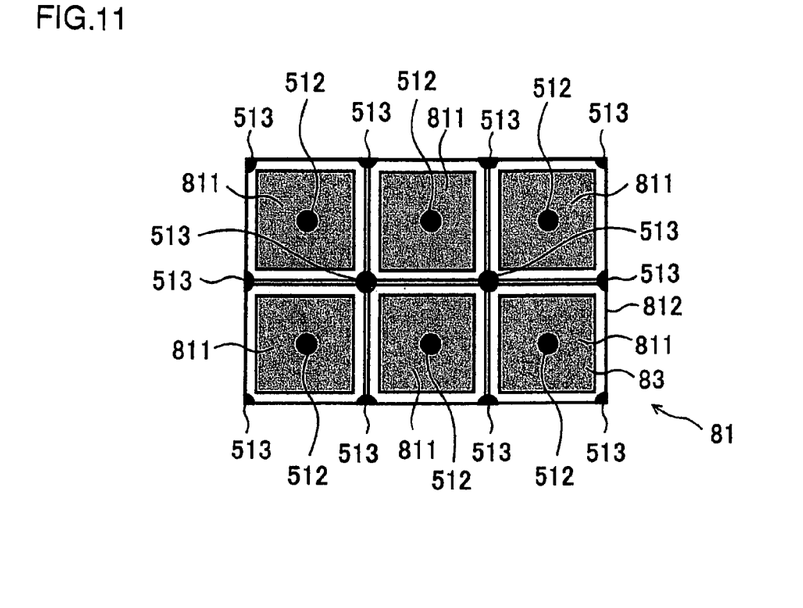
FIG. 11 shows a pattern of a part of an additional wiring layer in a dosimetry device for charged particle radiation according to a fifth embodiment of the invention.

According to a fifth embodiment, another additional wiring layer 81 is provided to the third or fourth embodiment. The additional wiring layer 81 is provided between the second wiring layer 52 and the third wiring layer 53 in the third or fourth embodiment.

FIG. 11 is a view of the additional wiring layer 81. The additional wiring layer 81 has a plurality of integrating capacitor electrodes 811 and a ground electrode pattern 812. The plurality of integrating capacitor electrodes 811 are formed as many as the number A of the plurality of first electrodes 21 and provided isolated from one another in a matrix. The integrating capacitor electrodes 811 are formed in positions opposing the first electrodes 21 and connected to the first electrodes 21 by the first through holes 512.

The ground electrode pattern 812 is formed in a mesh form to surround the integrating capacitor electrodes 811. The ground electrode pattern 812 is formed with a distance apart and around the integrating capacitor electrodes 811 and insulated from the integrating capacitor electrodes 811. The ground electrode pattern 812 is connected with the ground electrode patterns 511 (FIG. 5) and 512 (FIG. 6) by a plurality of second through holes 513. Consequently, the integrating capacitors 83 are formed between the integrating capacitor electrodes 811 and the ground electrode pattern 812, so that the integrating capacitors 83 are connected to the plurality of first electrodes 21 through the first through holes 512.

According to the fifth embodiment, the plurality of integrating capacitors 83 are formed in the additional wiring layer 81, the plurality of integrating capacitors 83 are connected to the plurality of first electrodes 21 and therefore the integrating capacitors 43 for the n-th wiring layer 5n may be omitted, so that the number of components in the signal processing blocks 40 at the n-th wiring layer 5n may be reduced. Therefore, a more inexpensive and reliable dosimetry device for charged particle radiation can be provided.

Sixth Embodiment

Figure 12:
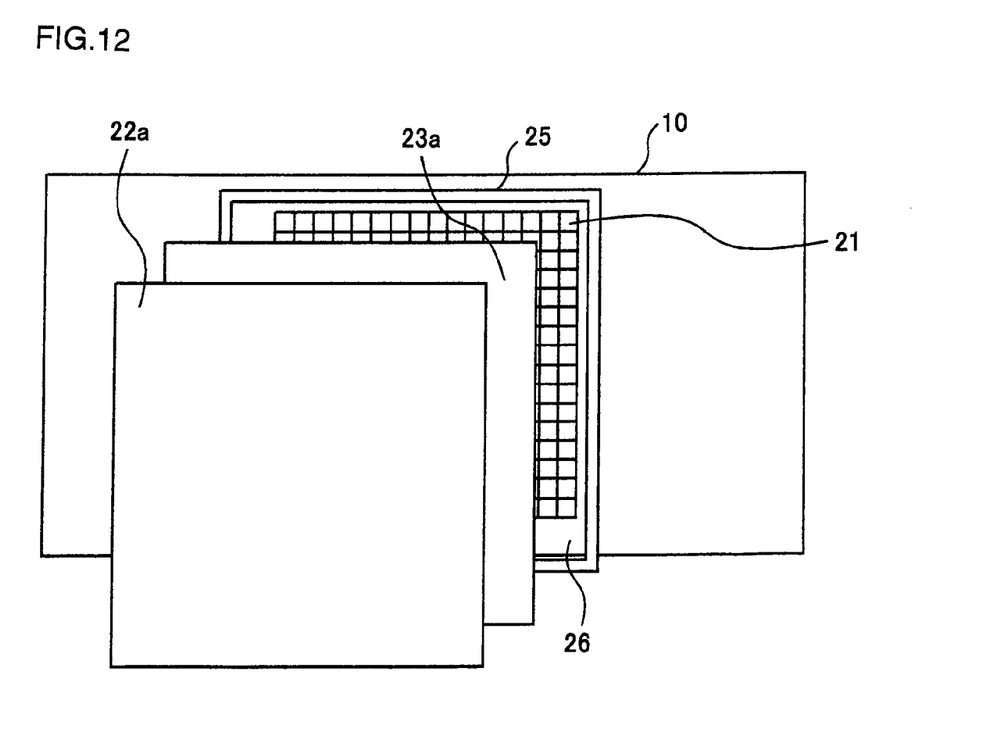
FIG. 12 is a view of a dosimetry device for charged particle radiation according to a sixth embodiment of the invention.

According to a sixth embodiment, in the first or third embodiment, the second electrode substrate 22 is made of a resin plate 22a having a transmittance to charged particle radiation equivalent to that of water, and the second electrode 23 is made of a thin metal film 23a.

FIG. 12 is a view of a dosimetry device for charged particle radiation according to the sixth embodiment. The thin metal film 23a is substantially equal to the resin plate 22a in size and adhered to one surface of the resin plate 22a. The resin plate 22a is fixed on the spacing frame 25 together with the thin metal plate 23a, and an ionized space 26 is formed between the thin metal plate 23a and the plurality of first electrodes 21. The outer circumference of the ionized space 26 is sealed by the spacing frame 25.

Figure 13:
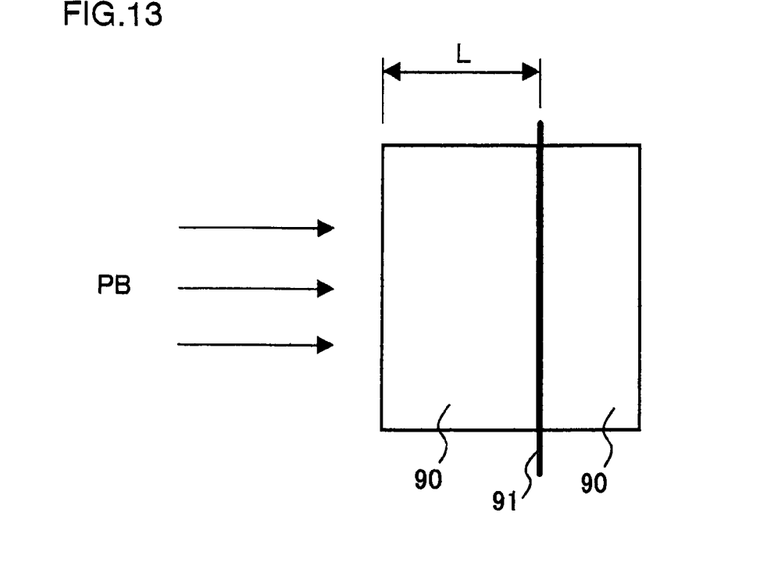
FIG. 13 is a view for illustrating a method of measuring a dose distribution in a medial application.

As shown in FIG. 13, in a dosimetry device for charged particle radiation for medical use, a dose distribution must be measured at a dose distribution measuring plane 91 that has a precise size L in the depth-wise direction in a phantom 90 having a transmittance to charged particle radiation equivalent to a human body in the direction of incidence of a charged particle beam PB. According to the sixth embodiment, if the thickness of the thin metal electrode 23a can be ignored as being equivalent to the thickness of a human body, the thickness of the air layer in the ionized space 26 formed between the metal electrode 23a and the plurality of first electrodes 21 can be ignored as being equivalent to the thickness of a human body. Therefore, the size from the surface of the resin plate 22a on the side away from the first electrodes 21 to the first electrodes 21 is evaluated as being equivalent to the thickness of a human body and can be considered as being equal to the thickness of the resin plate 22a. The thickness of the resin plate 22a can be measured with high precision when the dosimetry device for charged particle radiation is manufactured.

According to the sixth embodiment, the intermediate position between the opposing thin metal film 23a and the first electrodes 21 is the dose distribution measuring plane 91, and therefore the thickness produced by adding the thickness of the resin plate 22a to the thickness of the phantom 90 from the plane of incidence of the charged particle radiation to the dosimetry device is equal to the depth from the plane of incidence of the charged particle radiation to the dose distribution measuring plane 91. Therefore, according to the sixth embodiment, a dosimetry device for charged particle radiation capable of accurately determining the position of the dose distribution measuring plane in the depth-wise direction can be provided. Note that the resin plate 22a and the thin metal film 23a according to the sixth embodiment may be applied to the second, fourth, and fifth embodiments other than the first and third embodiments.

Seventh Embodiment

Figure 14:
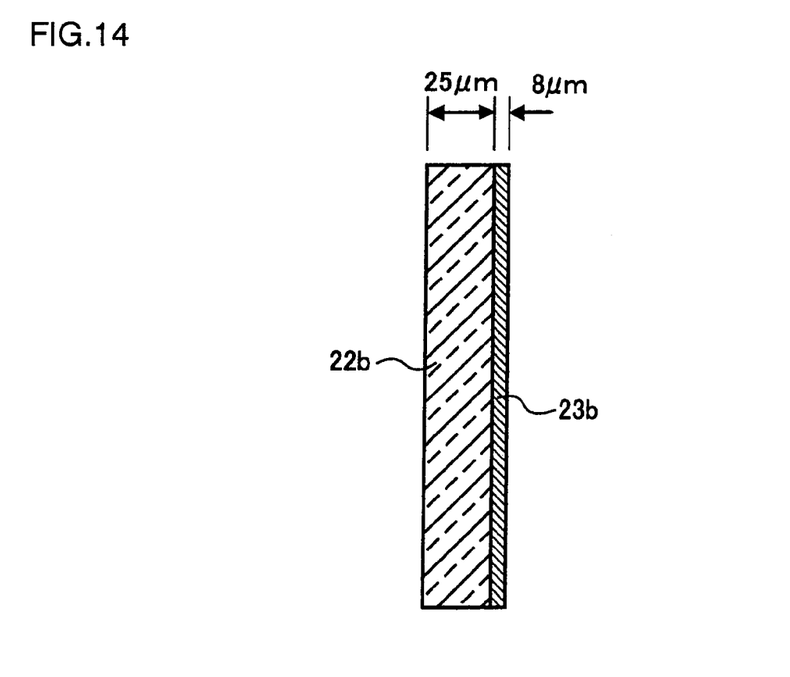
FIG. 14 is a sectional view of a second electrode substrate used in a dosimetry device for charged particle radiation according to a seventh embodiment of the invention.

According to a seventh embodiment, the second electrode substrate 22 according to the first or third embodiment is made of a polyimide flexible substrate 22b, and the second electrode 23 is for example made of a thin metal film 23b such as a thin copper film.

FIG. 14 is a sectional view of the polyimide flexible substrate 22b and the thin metal film 23b used according to the seventh embodiment. More specifically, the polyimide flexible substrate 22b has a thickness of 25 im. The thin metal film 23b for example is a thin copper film having a thickness of 8 im and is formed on one surface of the polyimide flexible substrate 23b by adhesion or vapor deposition. The polyimide flexible substrate 22b is fixed on the spacing frame 25 together with the thin metal film 23b, and an ionized-space 26 is formed between the thin metal plate 23b and the plurality of first electrodes 21. The outer circumference of the ionized space 26 is sealed by the spacing frame 25.

The polyimide flexible substrate 22b with a thickness of 25 im and the thin metal film 23b of a thin copper film with a thickness of 8 im formed thereon as shown in FIG. 14 is evaluated in thickness as the equivalent of 60 im of a human body. When a charged particle beam PB is directed upon a human body, the precision of the reaching depth of the charged particle beam needs only be about 1 mm, and therefore an error caused by the polyimide flexible substrate 22b having the thin metal film 23b formed thereon as shown in FIG. 14 is insignificant. According to the seventh embodiment, using the general purpose, inexpensive polyimide flexible substrate 22b, errors in the measuring precision are insignificant, and an inexpensive dosimetry device for charged particle radiation can be provided. Note that the polyimide flexible substrate 22b and the thin metal film 23b according to the seventh embodiment can be applied to the second, fourth, and fifth embodiments other than the first and third embodiments.

Eighth Embodiment

Figure 15:
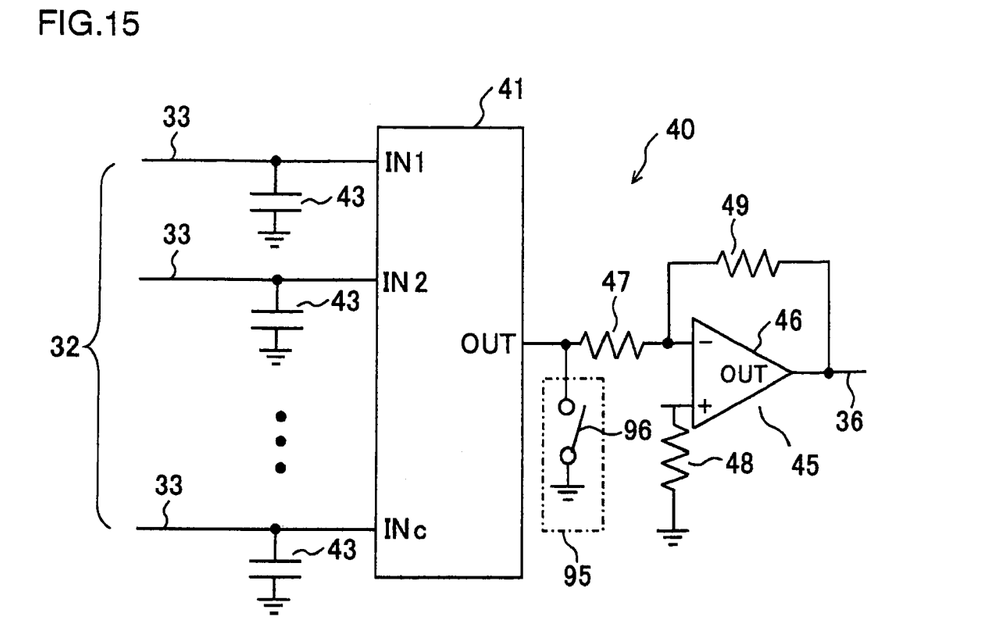
FIG. 15 is an electrical circuit diagram of one signal processing block in a signal processing circuit in a dosimetry device for charged particle radiation according to an eighth embodiment of the invention.

According to an eighth embodiment, the plurality of signal processing blocks 40 included in the signal processing circuit 30 according to the first or third embodiment are each provided with a discharge circuit 95 used to discharge the integrating capacitors 43.

FIG. 15 shows one signal processing block 40 in the signal processing circuit 30 according to the eighth embodiment. The discharge circuit 95 is provided in a circuit that grounds the output terminal OUT of the selector switch 41. The discharge circuit 95 includes a discharge switch 96. The discharge circuit 95 is turned off when the dose distribution of charged particle radiation is measured and does not discharge the integrating capacitors 43. The discharge circuit 95 reads out charge at all the first electrodes 21 by the signal processing circuit 30, is turned on after the measurement of the dose distribution of the charged particle radiation is completed, and then discharges the integrating capacitors 43 corresponding to the selector switch 41 to be ready for the next measurement.

According to the eighth embodiment, the discharge circuit 95 is provided at the output terminal OUT of each of the selector switches 41 in the signal processing circuit 30, and therefore the discharge circuit 95 does not have to be provided for each of the plurality of integrating capacitors 43, so that a more compact and inexpensive dosimetry device can be provided.

The arrangement in which the discharge circuit 95 is connected to the output terminal OUT of each of the selector switches 41 according to the eighth embodiment can be applied to the second, fourth, fifth, sixth, and seventh embodiments other than the first and third embodiments. According to the fifth embodiment, the integrating capacitors 83 connected to the first electrodes 21 are formed in the additional wiring layer 81, while in the fifth embodiment, the connection of the discharge circuit 95 to the output terminal OUT of each of the selector switches 41 allows the integrating capacitors 83 to be discharged after the dose distribution measurement.

Ninth Embodiment

Figure 16:
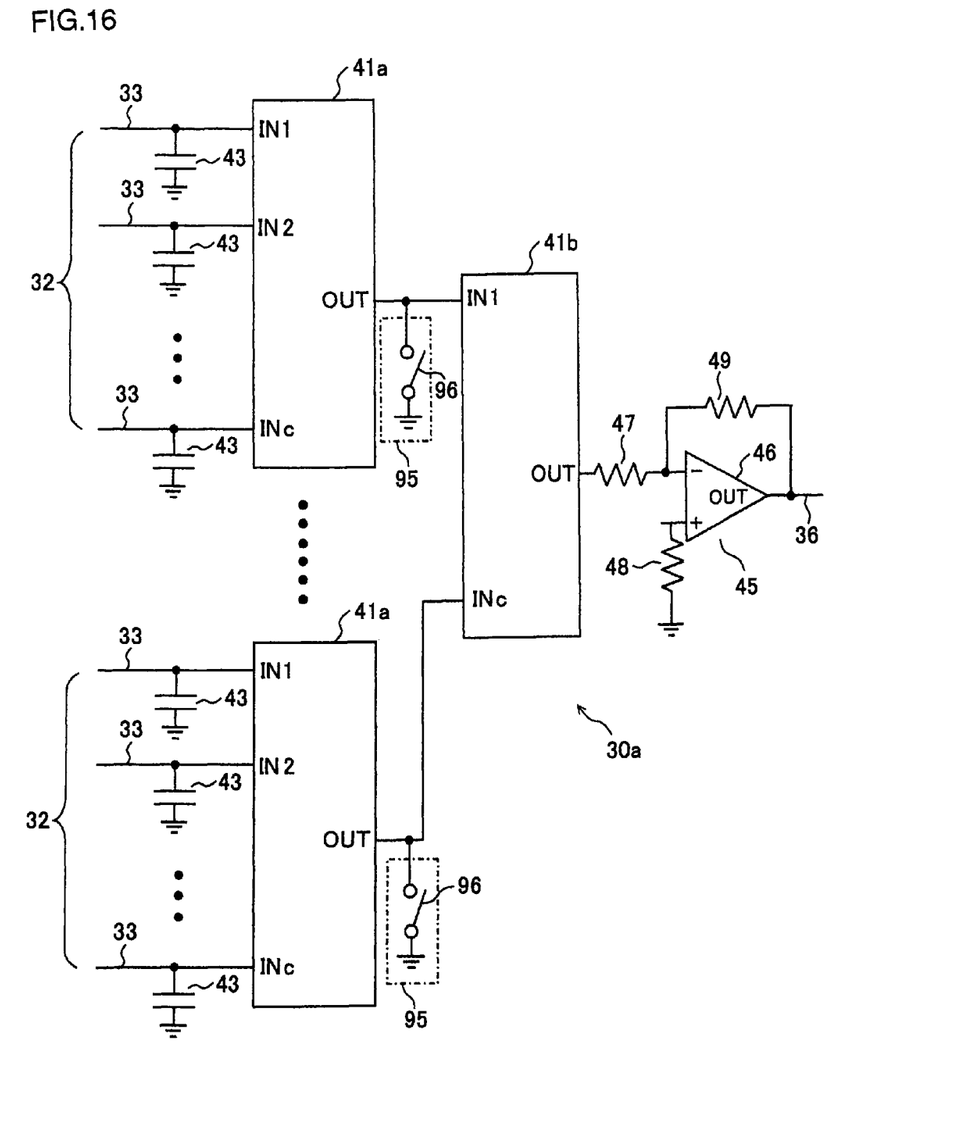
FIG. 16 is an electrical circuit diagram of a signal processing circuit in a dosimetry device for charged particle radiation according to a ninth embodiment of the invention.

According to a ninth embodiment, the signal processing circuit 30 according to the first or third embodiment is replaced by a signal processing circuit 30a.

FIG. 16 shows the signal processing circuit 30a used in the ninth embodiment. As shown in FIG. 16, the signal processing circuit 30a has a cascaded connection of a plurality of preceding selector switches 41a and a succeeding selector switch 41b. The outputs of the preceding selector switches 41a are sequentially switched by the succeeding selector switch 41b and connected to a common amplifying circuit 45. The plurality of preceding selector switches 41a each have C input terminals IN1, IN2, . . . , and INc and one output terminal OUT, and the input terminals IN1, IN2, . . . , and INc of each of the preceding selector switches 41a are connected to C different first electrodes 21 among the plurality of first electrodes 21. The input terminals IN1, IN2, . . . , and INc of the preceding selector switches 41a are connected to integrating capacitors 43 and the output terminals OUT of the preceding selector switches 41a are each connected with a discharge circuit 95 the same as that shown in FIG. 15.

If the number of the preceding selector switches 41a is B, the preceding selector switch 41b has B input terminals IN1, IN2, . . . , and INb and one output terminal OUT, and the input terminals IN1, IN2, . . . , and INb are connected to the output terminals OUT of the preceding selector switches 41a. The output terminal OUT of the succeeding selector switch 41b is connected to the common amplifying circuit 45. Similarly to the amplifying circuit 45 shown in FIG. 3, the amplifying circuit 45 includes an operational amplifier 46 and three resistors 47, 48, and 49, and the output terminal OUT of the operational amplifier 45 is connected to one external terminal 35.

According to the ninth embodiment, the outputs of the output terminals OUT of the preceding selector switches 41a are sequentially switched by the succeeding selector switch 41b and amplified by the common amplifying circuit 45, so that the number of the amplifying circuits 45 in the signal processing circuit 30a can be reduced, and the number of external terminals 35 can be reduced. Since the discharge circuit 95 is connected to the output terminal OUT of each of the preceding selector switches 41a, it is not necessary to provide the discharge circuits 95 corresponding to the plurality of integrating capacitors 43 similarly to the eighth embodiment, and a more compact and inexpensive dosimetry device can be provided.

Note that according to the ninth embodiment, the number B of the preceding selector switches 41a may be at least 2, and the number of the amplifying circuits 45 and the number of the external terminals 35 can still be reduced in this case as compared to the case of connecting the amplifying circuit 45 to each of the preceding selector switches 41a. If a plurality of such succeeding selector switches 41b are provided corresponding to a plurality of such preceding selector switches 41a, the number of the selector switches as a whole can be reduced.

The cascaded connection of the selector switches 41a and 41b according to the ninth embodiment can be applied to the second, fourth, fifth, sixth, and seventh embodiments other than the first and third embodiments. According to the fifth embodiment, an integrating capacitor 83 connected to each of the first electrodes 21 is provided in the additional wiring layer 81, but the multi-stage connection of the selector switches 41a and 41b according to the ninth embodiment may be applied to the fifth embodiment, and the discharge circuit 95 may be connected to the output terminal OUT of each of the preceding selector switches 41a, so that the integrating capacitors 83 may be discharged after the dose distribution measurement.

The dosimetry device for charged particle radiation according to the invention may be applied to a charged particle irradiation apparatus for medical use.

Various modifications and alterations of this invention will be apparent to those skilled in the art without departing from the scope and sprit of this invention, and it should be understood that this is not limited to the illustrative embodiments set forth herein.

What is claimed is:

1. A dosimetry device for charged particle radiation comprising:
   a printed circuit board having one surface and other surface opposing to each other, the one surface including a central region, and the other surface including a first portion that overlaps the central region of the one surface and a second portion positioned out side of the first portion so as to not overlap the central region;
   a plurality of first electrodes formed on the central region of the one surface of the printed circuit board;
   a spacing frame disposed on the one surface of the printed circuit board to surround the central region of the one surface;
   a second electrode substrate disposed on the spacing frame and having a second electrode opposing to each of the first electrodes through an ionized space; and
   a signal processing circuit disposed on the other surface of the printed circuit board,
   wherein the signal processing circuit includes a plurality of signal processing blocks each comprising:
      a plurality of integrating capacitors, coupled to the plurality of first electrodes, for integrating charge at each of the first electrodes;
      at least one amplifying circuit; and
      at least one selector switch that switchably connects each corresponding one of the integrating capacitors to the amplifying circuit,
      wherein the plurality of integrating capacitors are disposed on the second portion of the other surface of the printed circuit board.

2. The dosimetry device for charged particle radiation according to claim 1, wherein the second electrode substrate is constructed by a resin plate having a particle radiation transmitting characteristic equivalent to water.

3. The dosimetry device for charged particle radiation according to claim 1, wherein the second electrode substrate is constructed by a polyimide flexible substrate.

4. The dosimetry device for charged particle radiation according to claim 1, wherein a discharge switch is connected to the selector switch for discharging the integrating capacitors.

5. The dosimetry device for charged particle radiation according to claim 1, wherein the signal processing circuit has the first, second, and third selector switches, and each of the first and second selector switches switchably connects each corresponding one of the integrating capacitors to the third selector switch, and
   the third selector switch switchably connects the outputs of the first and second selector switches to the amplifying circuit.

6. The dosimetry device for charged particle radiation according to claim 5, wherein discharge switches are connected to the output sides of the first and second selector switches for discharging the integrating capacitors.

7. The dosimetry device according to claim 1, wherein a number of integrating capacitors equals a number of first electrodes, and each integrating capacitor is connected to a corresponding one of the plurality of first electrodes.

8. A dosimetry device for charged particle radiation comprising:
   a printed circuit board having one surface and other surface opposing to each other, the one surface including a central region, and the other surface including a first portion that overlaps the central region of the one surface and a second portion positioned out side of the first portion so as to not overlap the central region;
   a plurality of first electrodes formed on the central region of the one surface of the printed circuit board;
   a spacing frame disposed on the one surface of the printed circuit board to surround the central region of the one surface;
   a second electrode substrate disposed on the spacing frame and having a second electrode opposing to each of the first electrodes through an ionized space; and
   a signal processing circuit disposed on the other surface of the printed circuit board,
   wherein the signal processing circuit includes a plurality of signal processing blocks each comprising:
      a plurality of integrating ceramic capacitors resistant to charged particle radiation, coupled to the plurality of first electrodes, for integrating charge at each of the first electrodes;
      at least one amplifying circuit; and
      at least one selector switch that switchably connects each corresponding one of the integrating capacitors to the amplifying circuit,
      wherein the plurality of integrating ceramic capacitors are disposed on the first portion of the other surface of the printed circuit board, the first portion is a back surface of the first electrodes.

9. A dosimetry device for charged particle radiation comprising:
   a multi-layer printed circuit board having three or more wiring layers including at least first wiring layer, n-th wiring layer and a plurality of intermediate wiring layers between the first wiring layer and the n-th wiring layer opposing to one another, the multi-layer printed circuit board having one surface positioned on the first wiring layer and other surface positioned on the n-th wiring layer;
a plurality of first electrodes formed on the one surface on the first wiring layer;
a second electrode substrate having a second electrode opposing to each of the first electrodes through an ionized space; and
a signal processing circuit including a plurality of signal processing blocks,
wherein each of the signal processing blocks comprising:
a plurality of integrating capacitors, coupled to the correspondent electrodes of the plurality of first electrodes, for integrating charge at them;
at least one amplifying circuit disposed on the n-th wiring layer; and
at least one selector switch disposed on the n-th wiring layer that switchably connects each corresponding one of the integrating capacitors to the amplifying circuit,
wherein each of the plurality of signal processing blocks comprises a wiring combination for connecting the selector switch to corresponding one of integrating capacitors, and
wherein each wiring combination of the plurality of signal processing blocks is disposed on a different one of the intermediate wiring layers in the multi-layer printed circuit board.

10. The dosimetry device for charged particle radiation according to claim 9, wherein each of the wiring combinations connects each of the first electrodes in the corresponding group of first electrodes to the selector switch by through hole in the multi-layer printed circuit board.

11. The dosimetry device for charged particle radiation according to claim 10, wherein the multi-layer printed circuit board includes second wiring layer adjacent to the first wiring layer between the first wiring layer and the intermediate wiring layers, and a ground electrode pattern is formed on the second wiring layer.

12. The dosimetry device for charged particle radiation according to claim 11, wherein the multi-layer printed circuit board includes a plurality of additional wiring layers, each of the additional wiring layers is disposed between adjacent two of the intermediate wiring layers respectively, each of the additional wiring layers has a ground electrode pattern.

13. The dosimetry device for charged particle radiation according to claim 11, wherein the multi-layer printed circuit board includes a third wiring layer adjacent to the second wiring layer between the second wiring layer and the intermediate wiring layers,
a plurality of capacitor electrodes connected to the plurality of first electrodes are formed in the third wiring layer, and each of the capacitor electrodes forms the integrating capacitor.

14. The dosimetry device for charged particle radiation according to claim 9, wherein the second electrode substrate is constructed by a resin plate having a particle radiation transmitting characteristic equivalent to water.

15. The dosimetry device for charged particle radiation according to claim 9, wherein the second electrode substrate is constructed by a polyimide flexible substrate.

16. The dosimetry device for charged particle radiation according to claim 9, wherein a discharge switch is connected to the selector switch for discharging the integrating capacitors.

17. The dosimetry device for charged particle radiation according to claim 9, wherein the signal processing circuit has the first, second, and third selector switches, each of the first and second selector switches switchably connects each corresponding one of the integrating capacitors to the third selector switch, and
the third selector switch switchably connects the outputs of the first and second selector switches to the amplifying circuit.

18. The dosimetry device for charged particle radiation according to claim 17, wherein discharge switches are connected to the output sides of the first and second selector switches for discharging the integrating capacitors.

19. The dosimetry device for charged particle radiation according to claim 9,
wherein when assuming that a number of the plurality of the first electrodes is A and a number of the plurality of the signal processing blocks is B, the wiring combination of each of the signal processing blocks includes a number $C=A/B$ of wirings for connecting the selector switch to a corresponding one of integrating capacitors.

20. A dosimetry device for charged particle radiation comprising:
a multi-layer printed circuit board having three or more wiring layers including at least a first wiring layer and an n-th wiring layer, which oppose one another, and a plurality of intermediate wiring layers between the first wiring layer and the n-th wiring layer, the multi-layer printed circuit board having one surface positioned on the first wiring layer and another surface positioned on the n-th wiring layer;
a number A of a plurality of first electrodes formed on the one surface positioned on the first wiring layer;
a second electrode opposing each of the first electrodes through an ionized space; and
a signal processing circuit disposed on the other surface positioned on the n-th wiring layer, the signal processing circuit including a plurality of amplifying circuits and a number B of a plurality of selector switches, each selector switch switchably connecting each of the first electrodes in a corresponding group that includes a number $C=A/B$ of the first electrodes among the number A of plurality of first electrodes to the corresponding amplifying circuit,
wherein a number D of a plurality of wirings connecting the number A of the plurality of first electrodes to the number B of the plurality of selector switches are divided into a number E of a plurality of wiring combinations, and the number E of the plurality of wiring combinations are scattered on the plurality of intermediate wiring layers, and
wherein the number D is equal to the number C and the number E is equal to the number B.

* * * * *